Figure 1:
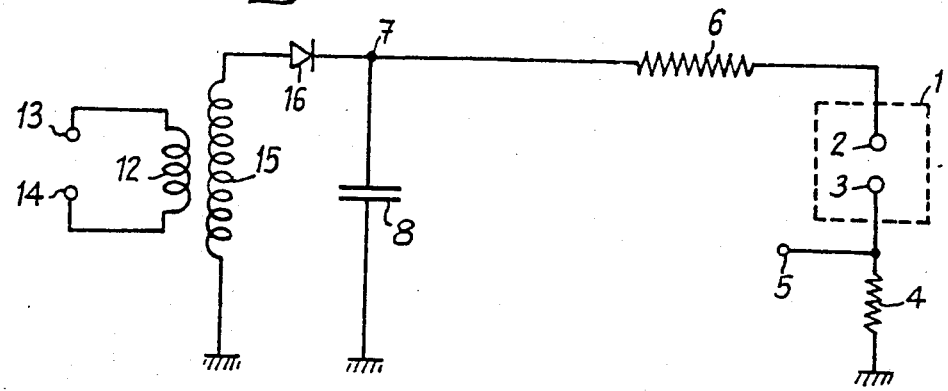
Figure 2:
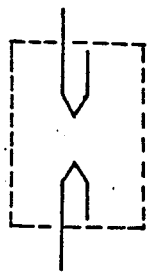
Figure 3:
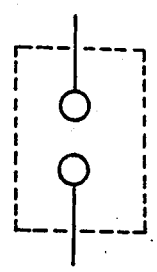
Figure 4:
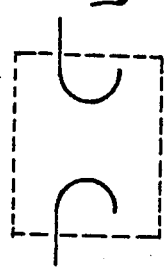

United States Patent [19]

Roos et al.

[11] Patent Number: 4,698,586

[45] Date of Patent: Oct. 6, 1987

[54] ELECTRIC PARTICLE DETECTOR FOR THE DETECTION OF FIRE

[75] Inventors: Andre Roos, Bonnieres; Daniel Dutertre-Laduree, Bonnieres/Siene; Max Goldman; Alice Goldman, both of Gif-sur-Yvette, all of France

[73] Assignee: PGEP Professional General Electric Corp., France

[21] Appl. No.: 807,879

[22] PCT Filed: Mar. 25, 1985

[86] PCT No.: PCT/FR85/00060

§ 371 Date: Jan. 27, 1986

§ 102(e) Date: Jan. 27, 1986

[87] PCT Pub. No.: WO85/04483

PCT Pub. Date: Oct. 10, 1985

[30] Foreign Application Priority Data

Mar. 26, 1984 [FR] France ................. 84 04645

[51] Int. Cl.⁴ .......................................... G01N 27/00

[52] U.S. Cl. .................................. 324/71.1; 324/464; 340/628

[58] Field of Search ............. 324/464, 468, 459, 71.1; 340/628, 629, 632, 577, 579; 250/374

[56] References Cited

U.S. PATENT DOCUMENTS

| | | | |
|---|---|---|---|
| 3,439,261 | 4/1969 | Loh et al. | 324/464 |
| 3,439,263 | 4/1969 | Broyle, Jr. | 324/459 |
| 3,728,615 | 4/1973 | Hill et al. | 324/464 |
| 4,121,105 | 10/1978 | Solomon | 250/381 |
| 4,336,455 | 6/1982 | Bryant | 340/629 |
| 4,538,137 | 8/1985 | Kimura | 340/629 |

Primary Examiner—Reinhard J. Eisenzopf
Assistant Examiner—Robert W. Mueller
Attorney, Agent, or Firm—Darby & Darby

[57] ABSTRACT

The sensor 1 has its point of operation towards the Townsend discharge zone, and the collection of ions causes an increase in the current passing through it. The electrodes of the sensor are formed by wires bent in the shape of an alpha.

6 Claims, 13 Drawing Figures

ELECTRIC PARTICLE DETECTOR FOR THE DETECTION OF FIRE

The invention relates to an electric particle detector for monitoring the atmosphere in buildings for example, especially for the detection of fires.

The problem of fire detection by the detection of ions is well known. Usually, the air in a room is ionized by means of a radioactive source or a periodic electric spark and the monitoring is carried out by measuring an ionic current. When there is a fire, heavy particles of smoke for example, are carried in the building to the detection chamber where they disturb the movement of ions by intercepting or blocking them. The ionic current measured then drops and this drop is used to set off an alarm. It should be noted that humidity also reduces the ionic current. To prevent the humidity from triggering false alarms, it is customary to provide a reference chamber that is protected from humidity, or to provide electronic compensation of the sensitivity of the detector. In this case it becomes very difficult to detect a smouldering fire, for example. In fact with fires which do not have a great release of heat, the currents of convection are not strong enough to transport the heavy particles to the detector within a reasonable time. Consequently, the response time of the detectors in the case of a smouldering fire is very long, and this is a drawback as regards safety regulations.

One of the objects of the present invention is to provide a detector in which, unlike known detectors, the presence of particles emitted by the start of a fire, for example, increases the current passing through the detector.

Another aim of the invention is to provide a detector of charged particles that is remarkably simple and is capable of operating from different types of supply with an extremely low consumption.

The invention relates to an electric particle detector of the type comprising a sensor with two electrodes supplied with electricity, characterised in that the said sensor has its operating point at a current of between $10^{-13}$ and $10^{-9}$ A, and in that the collection of ions by the said sensor causes an increase in the current passing through it.

According to other features of the invention:

the electrodes are formed by wires bent in the shape of the Greek symbol alpha ($\alpha$);

one of the electrodes of the sensor is connected to the point of supply via the intermediary of a resistor of very high value, while the other electrode is connected to the measurement point and, from there, to earth (ground) via the intermediary of a resistor;

when the sensor is in operation, the collection of ions causes an increase in current in the sensor;

the sensor is supplied via the intermediary of at least one diode which is arranged to operate at the start of its characteristic and behaves like a resistance;

the sensor is connected to the measurement point via the intermediary of a resistor of high value, each of the end terminals of this resistor being connected to earth (ground) by a capacitor of very low value;

the wires forming the alpha-shaped electrodes have barbs.

Figure 5:
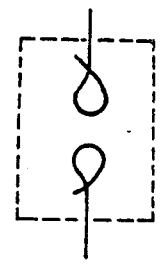
Figure 6:
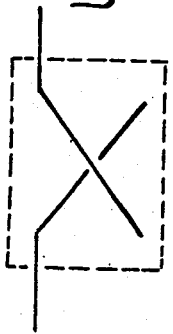
Figure 7:
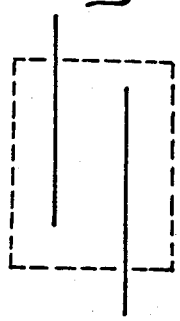
Figure 8:
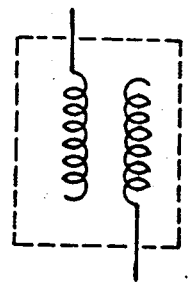
Figure 12:
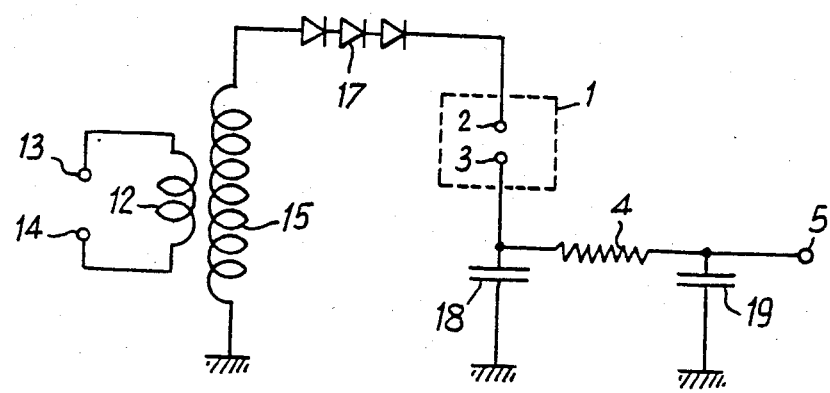
Figure 13:
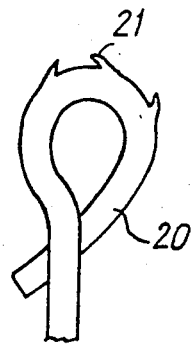

The following have been illustrated in the drawings by way of example:

FIG. 1: a simplified electrical diagram of one embodiment of a charged particle detector according to the invention;

FIGS. 2–11: various embodiments of the electrodes of the detector of FIG. 1;

FIG. 12: a variant of the electrical diagram of FIG. 1;

FIG. 13: an enlarged view of an alpha-shaped electrode according to FIG. 5.

Referring to the drawings, there is illustrated a sensor 1 for charged particles, which constitutes the sensitive portion of the detector. The housing of this sensor is not shown. This housing must be open to receive the gases liable to pass through it and preferably comprises a grille allowing the gases and charged particles emitted by the commencement of a fire to pass through. The electrodes 2 and 3 of the sensor 1 will be described hereinafter.

The sensor 1 is connected to earth (ground) by a resistor 4 the value of which is, for example, of the order of 10 megohms.

There is provided between the sensor 1 and the resistor 4 a first measurement point 5. The sensor 1 is connected to a power supply via the intermediary of a series resistor 6 of very high value of the order of 1 gigohm. The supply source is designated by the point 7. It is decoupled from earth (ground) by a capacitor 8.

The power supply of the circuit is represented by a step-up transformer of which the primary winding 12 is supplied between the terminals 13, 14 and of which the secondary winding 15 is connected between on the one hand earth and the point 7 via the intermediary of a diode 16 on the other hand.

It should be specified that the power supply voltage of the circuit may be continuous, at point 7, with a voltage of the order of 1000 volts, for example; that the voltage at point 7 may be rectified, as shown in the diagram of FIG. 1, the primary winding of the transformer being supplied by alternating current; and finally that it may be in pulses, which may be true in the case in FIG. 1, the primary winding thus being supplied by pulses coming, for example, from the discharge of a capacitor.

Taking into account the value of the resistor 6, and the value of the supply voltage, the current likely to pass through the sensor 1 is of the order of $10^{-9}$ to $10^{-12}$ A. The point of operation of the sensor must be below the non-maintained discharge zone, that is to say well below, in intensity, the self-maintained avalanche zone corresponding to the corona effect.

It can be seen from FIG. 12 that the resistor 6 of FIG. 1 has been replaced by diodes 17 which operate at the start of the characteristic and behave like a resistor of high value. This arrangement has a current-regulating effect in order to increase the voltage across the sensor as a function of aging. The capacitor 8 of FIG. 1 has also been omitted from the circuit illustrated by FIG. 12. On the other hand, the measurement point 5 is returned after the resistor 4 of high value, the two end terminals of which are connected to earth (ground) via the intermediary of two capacitors 18 and 19 of very low value. In this manner an integrated current output of the order of $10^{-11}$ A is obtained.

Figure 9:
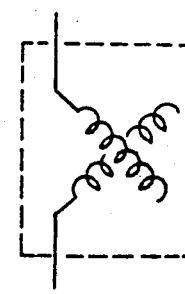
Figure 10:
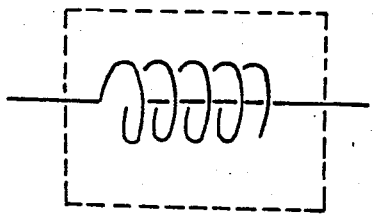
Figure 11:
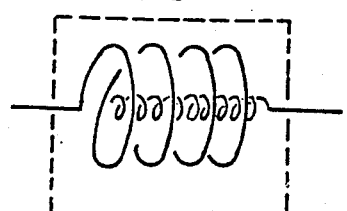

The shape of the electrodes 2, 3 is provided for the purpose of limiting the electric field between them so as to avoid any discharge. This is why the electrodes are not formed by points opposite one another but rather by fingers (FIG. 2), balls (FIG. 3), wires bent in a semi-circle (FIG. 4) or in the shape of an alpha (FIG. 5), or by straight wires arranged in parallel planes (FIG. 6), the projection of one of the wires on the plane of the other wire intersecting the latter, parallel wires that is, straight wire disposed side by side along a parallel axes (FIG. 7), helical wires arranged in parallel (FIG. 8) or in parallel planes (FIG. 9). It is also possible to have one of the electrodes in the shape of a coil distributed on a cylinder and the other electrode arranged along the axis of the cylinder, either in straight form (FIG. 10) or in the form of a helix (FIG. 11). These embodiments of the electrodes are described only by way of illustration.

Preferably, the electrodes are in the form of wire bent, for example, in the shape of an alpha, according to the diagram of FIG. 5.

In FIG. 13, the alpha-shaped electrode is shown in the form of a bent wire 20. This wire is not perfect and carries barbs indicated by 21, since the microgeometry of the wire is useful as regards questions of electrical field. By way of example, a wire of 100 μm diameter is bent with a radius of curvature less than or equal to 1 mm.

This shape of electrode proves particularly efficient for collecting charged particles not completely burned that are emitted by a fire and especially by a smouldering fire. When these particles are collected by the electrodes they are discharged there, which creates a current, but they are ignited there again, which causes an emission of secondary ions which are also collected, from which there results a net increase in current. This secondary combustion is improved by making the electrodes from, or covering them with, special alloys or metals.

In certain cases a non-charged particle, such as dust, is deposited on an electrode. If an ion comes to rest on the dust particle there is produced between this ion and the electrode a discharge, which corresponds to an avalanche multiplication of electric charges, and a greater current appears. Furthermore, this discharge is accompanied by a reaction equivalent to a chemical reaction of oxidation of the dust particle, the result of which is combustion of the dust, that is to say, cleaning of the electrode.

There results from this an improvement in the sensitivity of the sensor and automatic cleaning of the electrodes: the sensor can thus operate at a lower supply voltage.

The fundamental difference in relation to conventional ionic sensors is that in the sensor according to the invention the collected ions and the secondary ions, also collected, increase the current in the sensor. On the other hand, variations in the ambient temperature, air currents and the presence of non-charged particles do not have any perceptible influence on the current in the sensor, which avoids false alarms.

Returning to the diagram of FIG. 1, it is possible to analyse the operation of the detector in the following simplified manner: in the absence of ions, the measurement point 5 is at a stable potential; in the presence of collected ions, the current in the sensor rises and the potential of this point 5 varies.

The power supply to the sensor may be continuous, rectified alternating, or pulsed with sampling pulses of the order, for example, of 10 to 20 ms per second.

The invention is especially well suited to the detection of the start of fires, especially smouldering fires, by means of its sensor which senses the small charged particles emitted on commencement of a fire. It is equally well suited to the detection of smoke, gas, vapours (of sodium, for example), dusts, aerosols or ions.

We claim:

1. An electric particle detector, which comprises:
   a sensor (1) for detecting the presence of charged particles in the vicinity of the detector, the sensor having a pair of spaced apart first and second electrodes (2, 3), each of the first and second electrodes having the shape of the Greek symbol alpha ($\alpha$) to limit the electric field between the first and second electrodes and to minimize electrical discharge therebetween; and
   means for providing an operating current to the sensor of between about $10^{-9}$ amperes and about $10^{-13}$ amperes, said current being below the current necessary for self-sustained avalanche, wherein the presence of charged particles causes the current through the sensor to increase.

2. An electric particle detector as defined by claim 1, wherein each of the alpha-shaped first and second electrodes is formed as a bent wire and includes barbs (21) projecting from the periphery of the wire for collecting charged particles.

3. An electric particle detector as defined by claim 1, wherein the current providing means includes first resistive means (6) electrically coupled to the first electrode (2), and wherein the detector further includes second resistive means (4) electrically coupled to the second electrode (3).

4. An electric particle detector as defined by claim 3, wherein the first resistive means is a resistor having a resistance of about 10 gigohms, and the second resistive means is a resistor having a resistance of about 10 megohms.

5. An electric particle detector as defined by claim 1, wherein the current providing means includes at least one diode (17) electrically coupled to the first electrode (2).

6. An electric particle detector as defined by claim 1, wherein the detector further includes a resistor (4) electrically coupled to the second electrode (3), the resistor having first and second end terminals, and first and second capacitors (18, 19) electrically coupled to the first and second end terminals of the resistor (4), respectively.

* * * * *